United States Patent [19]

Berson

[11] Patent Number: 4,586,921

[45] Date of Patent: May 6, 1986

[54] METHOD OF APPLYING A LOCAL ANESTHETIC AGENT TO A WOUND

[76] Inventor: Daniel Berson, 6 Rollingwood Dr., New City, N.Y. 10956

[21] Appl. No.: 523,929

[22] Filed: Aug. 17, 1983

[51] Int. Cl.⁴ .......................................... A61M 31/00
[52] U.S. Cl. ..................................................... 604/49
[58] Field of Search ............................... 604/272–274, 604/158–170, 9, 247, 28, 49

[56] References Cited

U.S. PATENT DOCUMENTS

| | | | |
|---|---|---|---|
| 387,454 | 8/1888 | Siegenthaler | 604/164 |
| 2,257,369 | 9/1941 | Davis . | |
| 2,393,003 | 1/1946 | Smith | 604/170 |
| 2,531,667 | 12/1947 | Brent . | |
| 2,828,744 | 4/1958 | Hirsch et al. | 604/165 |
| 3,173,418 | 1/1961 | Baran . | |
| 3,312,220 | 4/1963 | Eisenberg . | |
| 3,399,674 | 7/1965 | Pannier et al. . | |
| 3,459,188 | 7/1965 | Roberts . | |
| 3,508,545 | 4/1970 | Reif et al. . | |
| 3,539,034 | 11/1970 | Tafeen | 604/164 |
| 3,572,333 | 3/1971 | Hubert | 604/170 |
| 3,598,119 | 8/1971 | White . | |
| 3,670,729 | 6/1972 | Bennett et al. . | |
| 3,680,562 | 8/1972 | Wittes et al. . | |
| 3,698,396 | 10/1972 | Katerndahl et al. | 604/164 |
| 3,885,561 | 5/1975 | Cami | 604/247 |
| 3,890,970 | 6/1975 | Gullen | 604/170 |
| 4,037,599 | 7/1977 | Raulerson . | |

FOREIGN PATENT DOCUMENTS

| | | | |
|---|---|---|---|
| 945861 | 4/1974 | Canada | 128/127 |
| 563969 | 9/1977 | U.S.S.R. | 604/164 |

Primary Examiner—C. Fred Rosenbaum
Assistant Examiner—Mario Costantino
Attorney, Agent, or Firm—Ostrolenk, Faber, Gerb & Soffen

[57] ABSTRACT

A surgical device is provided for placement in a patient, e.g. percutaneous placement, for the application of a local anesthetic agent to a wound. The device comprises a catheter and obturator. The catheter is a flexible hollow tubular member, the distal end of which is closed and has thereon a cutting means for assisting in placement of the catheter in the patient. The proximal end is open and has a means thereon for permitting the injection of a liquid, e.g. a local anesthetic agent, into the tubular member. A plurality of openings are provided in the wall of the tube along its length for passage of the injected liquid therethrough. The obturator is a rigid elongated member having a diameter suitable for insertion into the catheter. The distal end of the obturator abuts the interior end of the catheter. The proximal end of the obturator has means thereon for engaging the proximal end of the catheter. The obturator is of a length sufficient to stiffen the catheter to permit placement of the catheter in the patient using the cutting means on the distal end of the catheter. The local anesthetic agent when injected into the catheter passes through the openings therein and is substantially evenly dispersed into the body tissue adjacent the wound to thereby cause analgesia of the wound.

3 Claims, 4 Drawing Figures

METHOD OF APPLYING A LOCAL ANESTHETIC AGENT TO A WOUND

BACKGROUND OF THE INVENTION

1. Field of the Invention

This invention relates to a catheter and obturator therefor which may be used for the application of a liquid along the length of a wound, and more particularly for the application of a local anesthetic agent along the length of the wound to cause analgesia of the wound.

2. Prior Art

After abdominal or other type surgery, analgesia is necessary for several days until operative wound pain has subsided. The most common analgesia used is a narcotic and/or a sedative which acts systemically, typically has undesirable side effects, such a respiratory depression, hypotension, nausea, paralytic ileus, clouding of sensorium and possible drug dependency. The drugs are usually given intramuscularly on a demand schedule, up to every three hours.

A preferred system of analgesia causes local blockage of the segmental nerves in the area of the operative wound using a long acting local anesthetic agent such as bupivacaine or etidacaine. These agents provide local analgesia for six hours or more when infiltrated into the area of the wound. Using known standard techniques, however, would require multiple needle injections of the local anesthic agent every six hours to provide continuous analgesia. Such a procedure is impractical and beyond the scope of customary nursing practice.

It is therefore highly desirable to provide analgesia of an operative wound without undesirable side effects of narcotics and sedatives by the use of a local anesthetic agent. It is further desirable to provide this local anesthetic agent to the operative wound continuously, or at the very least, intermittently, without the requirement for multiple needle injections. Additionally, such a procedure should be compatible with current surgical and nursing procedures.

Numerous catheter devices are known for various medical purposes, but none provides a device and/or method suitable for continuously or intermittently applying a local anesthetic agent to an operative wound to accomplish local blockade of multiple segemental nerves.

For example, U.S. Pat. No. 2,257,369 to Davis describes a combination catheter and drainage suitable for draining and medicating the bladder and the duct of the penis leading from the bladder cavity to the exterior through the penis. The catheter comprises an inner and outer tube, the outer tube having a plurality of ports or openings in the outer wall and communicating to the space between the inner and outer tube. The inner tube extends beyond the outer tube for a substantial distance to permit the inner tube to extend into the bladder cavity and permit drainage of the bladder cavity and irrigation.

U.S. Pat. No. 2,531,667 to Brent describes an apparatus for administering repeated injections. The apparatus comprises a syringe adapted to be strapped to the leg or arm of a patient, and which is provided with a flexible discharge tube adapted to dwell in a patient during the period of treatment. The flexible injection tube has an inlet end secured to the discharge end adapted to be inserted in a patient. The flexible injection tube or cannula is described as made of synthetic rubber, nylon or other flexible material and has a single discharge end inserted in a vein and remains in this position during treatment. The flexible tube is inserted into the vein by means of a trocar having a lumen slightly larger than the flexible tube. The trocar is first inserted in the vein and the flexible tube is slid through the trocar into its desired position in the vein and the trocar is then removed by sliding it backwardly over the flexible tube while holding the outer end of the tube to prevent its removal from the vein. This type device is unsuitable for the injection of local analgesia to an area of a patient.

U.S. Pat. No. 3,173,418 to Baran describes the use of a double-wall endotracheal cuff useful for continuous or intermittent local entracheal anesthesia through a perforated external cuff.

U.S. Pat. No. 3,312,220 to Eisenberg describes a plastic cannula which is designed to allow introduction into the patient over a steel needle. Following insertion of the plastic cannula the steel needle is withdrawn. The plastic cannula has a blunt tapered point at the leading end. The tapered end of the cannula is perforated with accessory drainage holes to forestall plugging should the tip of the cannula come in contact with the tissue surface or become plugged with proteinaceous material. The sharp steel needle permits the easy penetration of the cannula into the body wall.

U.S. Pat. No. 3,399,674 to Pannier et al describes a cannulated needle in telescopic association with the interior of a catheter. The needle projects out of the catheter on the distal end to facilitate venipuncture.

U.S. Pat. No. 3,459,188 to Roberts describes a catheter-stylet combination for puncturing a patients abdominal wall for peritoneal dialysis. A rigid wire stylet fits within a bore of a flexible plastic catheter and has a point on one end protruding from the catheter and a handle engaged on the opposite end of the catheter. The catheter has a larger internal bore than the stylets outer diameter and has a series of ports through the catheters wall extending from the one end to form a sieve portion permitting fluid to enter immediately after insertion. The stylet has an elongated piercing element which has a pointed end extending from the end of the catheter. When the stylet is withdrawn a large end port is provided in the catheter which precludes its use in the manner described herein.

U.S Pat. No. 3,598,119 to White and U.S. Pat. No. 3,508,545 to Reif et al describe catheter devices for placement within the body tissues with a retention means, to allow repeated injection of local anesthetic for paracervical anesthesia. These devices deliver the medication only at the catheter tip precluding their use to provide dispersion of a local anesthic agent along the length of an operative wound.

U.S. Pat. No. 3,670,729 to Bennett et al describes a transfusion needle having a sleeve which has a plurality of perforations which are spaced along its length to ensure the permanent flow of an anti-inflammatory fluid at the sight of entry of the transfusion needle. The device is used with a conventional steel needle having a sharp point inserted through the sleeve so that the point projects beyond the end of the sleeve. The needle with the device is then inserted into the patients vessel.

U.S. Pat. No. 3,680,562 to Wittes et al describes an apparatus for surgical catheter drainage which includes a flexible plastic tube inwardly curved at the distal end with tapered blunt tip and a longitudinally aligned outlet ports spaced on the inside of the curve at the distal end of the tube. within the tube is disposed a hollow piercing element having a bevelled point which extends beyond the distal end of the tube. The tapered blunt tip of the tube provides a close fit with the piercing element. The above assembly is inserted through the skin into the bladder and after being properly positioned, the piercing element is removed and the catheter tube is inserted into the bladder. As the piercing element is withdrawn from the catheter tubing, its distal end assumes a preformed coil or curve. This device does not permit the controlled dispersion of medicine along the length of the tube due to the open distal end.

U.S. Pat. No. 4,037,599 to Raulerson describes a continuous flow catheter device for intravascular placement during hemodialysis. This device does not permit even dispersion of a medication along a subcutaneous or muscular plane.

None of the foregoing catheter devices and assemblies are suitable for the continuous or intermittent application of a local anesthetic agent along the length of an operative wound over a long period of time. Additionally in all of the catheter devices the removable needle, trocar or stylet constitutes the piercing means necessitating the distal end of the catheter being open. Such an opening does not permit the even dispersion of the liquid passing therethrough.

OBJECTS AND SUMMARY OF THE INVENTION

It is an object of the present invention to provide a device and method suitable for application of a local anesthetic agent to an operative wound without necessitating the use of narcotics and sedatives which are accompanied by their undesirable side effects.

It is a further object of this invention to provide a local anesthetic agent to an operative wound continuously for several days without necessitating the use of multiple puncture wounds.

It is a further object of this invention to provide a system and method of applying a local anesthetic agent to an operative wound which is compatible with current surgical and nursing procedures.

All of the foregoing objects of this invention are obtained by a surgical device suitable for percutaneous placement in a patient for the application of a local anesthetic. The device comprises a catheter and obturator. The catheter is a flexible hollow tubular member, the distal end of which is closed and has thereon a cutting means for assisting in placement of the catheter in the patient. The proximal end is open and has a means thereon for permitting the injection of a liquid, e.g. a local anesthetic agent, into the tubular member. A plurality of openings are provided in the wall of the tube along its length for passage of the injected liquid therethrough. The obturator is a rigid elongated member having a diameter suitable for insertion into the catheter. The distal end of the obturator abutts the interior end of the catheter. The proximal end of the obturator has means thereon for engaging the proximal end of the catheter. The obturator is of a length sufficient to stiffen the catheter to permit placement of the catheter in the patient using the cutting means on the distal end of the catheter. The local anesthetic agent when injected into the catheter passes through the openings therein and is substantially evenly dispersed into the body tissue adjacent the wound to thereby cause analgesia of the wound.

BRIEF DESCRIPTION OF THE DRAWINGS

Other objects and advantages will become apparent from the following detailed description of the invention which is to be taken in conjunction with the accompanying drawings illustrating a preferred embodiment of the invention in which.

DETAILED DESCRIPTION OF THE INVENTION

Figure 1:
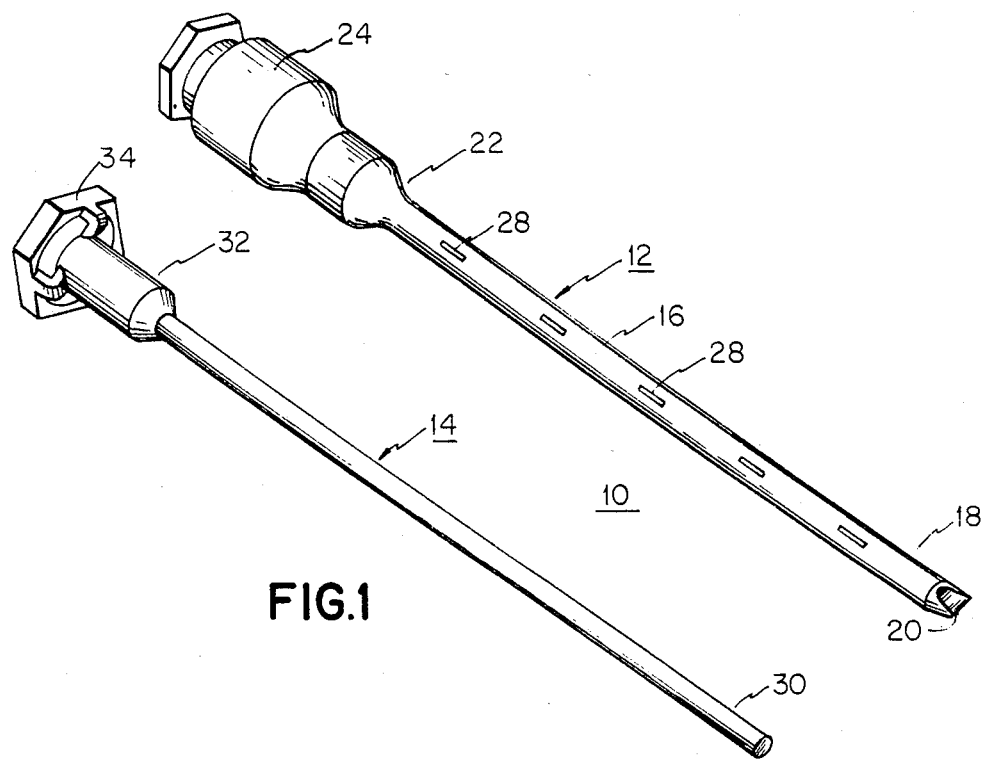
FIG. 1 is a perspective view of the catheter and obturator of the present invention.
Figure 2:
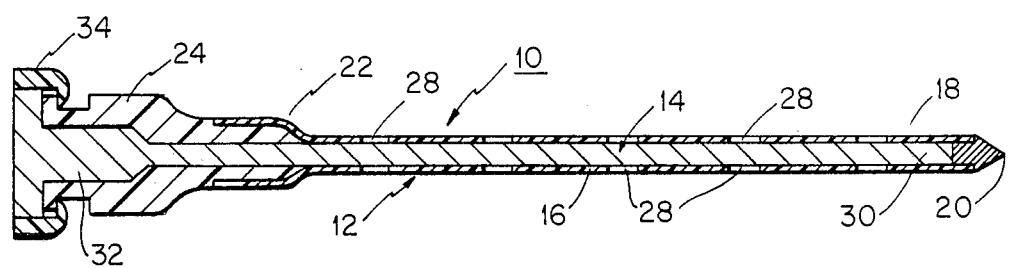
FIG. 2 is a cross-sectional view of the assembled catheter and obturator.

Referring more particularly to FIGS. 1 and 2 herein, the surgical device of this invention, generally designated (10) comprises a catheter (12) and an obturator (14). The catheter (12) comprises a flexible hollow tubular member (16). A silicone rubber is preferred for the catheter because it is flexible, sterilizable, and inert to the human body. The silicone rubber additionally presents a resilient material on which the flesh can take hold and releaseably secure the catheter in place. Other materials such as polypropylene, nylon, tetrafluoroethylene, commonly available under the trademark TEFLON, or any other suitable flexible material may be used.

Still referring to FIGS. 1 and 2, the tubular member (16) has a closed distal end (18) and has a cutting means, or tip (20) of metal or other similar type material. The cutting tip (20) is preferably a chisel tip configuration which is permanently affixed to the distal end of the tubular member (16). The cutting means (20) assists in the percutaneous placement of the catheter (12) in a patient.

Figure 3:
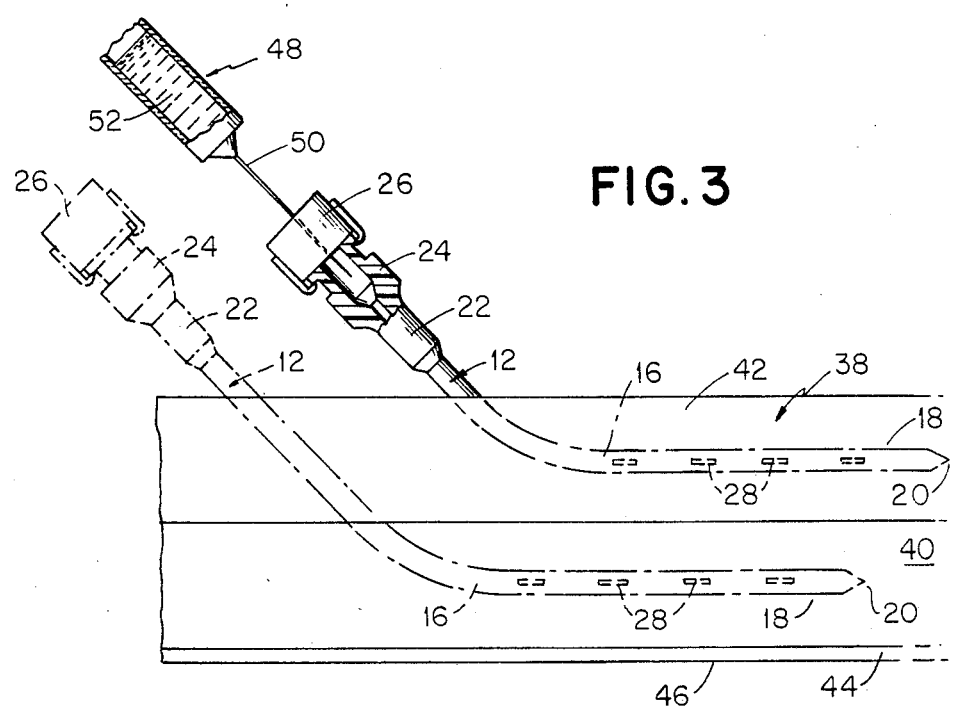
FIG. 3 is a longitudinal sectional view of a portion of the human abdominal wall depicting the method of application of a local anesthetic agent through the catheter.

An open proximal end (22) has a means thereon for permitting injection of a liquid, e.g. a local anesthetic agent, into the tubular member (16). Typically a rigid hub (24) is on the proximal end (22) and is in open communication with the interior of the tubular member (16) and in sealing engagement with the proximal end (22). Such hubs (24) are well known in the art and are typified by the standard female luer fitting which is permanently affixed to the ends of catheters. The hub is of the lock type and of standard size to accept currently used intravenous equipment and syringes. The hubs are constructed so as to allow easy disengagement from each other without fear of binding or locking. Optionally, as depicted in FIG. 3, a standard injection cap (26) may be utilized which matingly engages the hub (24).

Referring to FIGS. 1 and 2, the tubular member (16) is further provided with a plurality of openings (28), preferably in the form of slits, in the wall of the tubular member (16) along its length. These openings (28) permit the passage of the injected liquid, e.g. the local anesthetic agent, therethrough. For general guidance, these openings are disposed along the length of the tubular member (16) at approximately one centimeter intervals, although greater or lessor intervals may be utilized. Typically the catheter is a length of from 10 to 20 centimeters with a diameter of approximately 3.2 millimeters (outside diameter) although greater or lessor lengths and diameters may be utilized depending on the circumstances.

The obturator (14) is comprised of a rigid elongated member having a diameter suitable for insertion into the tubular member (16), i.e. the outside diameter of the obturator (14) of less than the inside diameter of the tubular member (16). The distal end (30) is designed to abutt onto the interior of the distal end (18) of the tubular member (16). This is depicted more clearly in FIG. 2. In effect the distal end of the obturator (30) abutts against the cutting tip (20) which is attached to the tubular member (16). The proximal end (32) of the obturator (14) has a means thereon for engaging the proximal end (22) of the tubular member (16). Typically, as depicted in FIGS. 1-2, the proximal end (32) of the obturator (14) has a hub (34) thereon which matingly engages the hub (24) on the tubular member (16).

The obturator is, perferably, of metal construction and of such a diameter so as to snuggly occlude the lumen of the tubular member (16). The length of the obturator (14) is sufficient to stiffen the catheter (12) to permit the percutaneous placement of the catheter (12) in the patient using the cutting means (20) on the distal end (18) of the catheter (12). Preferably the obturator (14) occludes the opening (28) in the walls of the tubular member (16) by blocking them with the obturator (14) body and/or closing the slits when the tubular member (16) is stretched and stiffened. Such occlusion of the openings prevents the blockage of the openings when the catheter assembly is being placed in a patient. Such a stiffening of the tubular member (16) is accomplished when the male luer fitting or hub (34) of the obturator is mated and locked to the female luer fitting or hub (34) of the catheter to thereby apply tension along the length of the tubular member (16).

Figure 4:
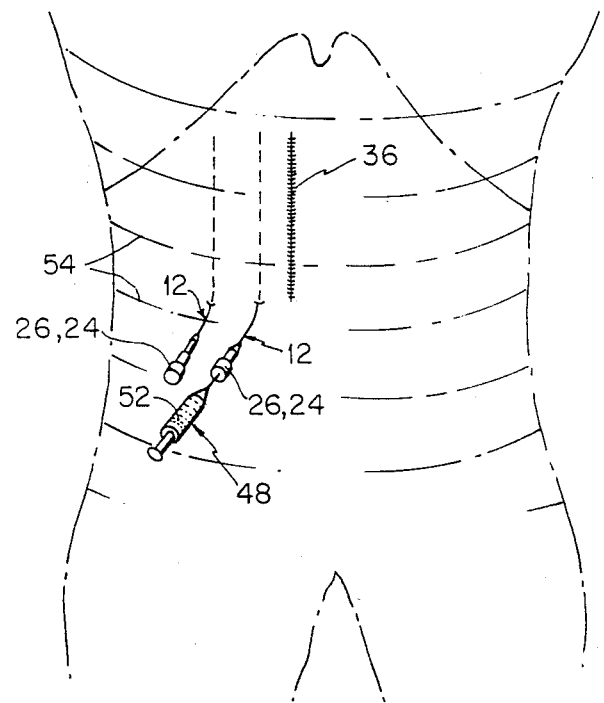
FIG. 4 is an anterior view of the human abdominal wall depicting a typical method of applying an anesthetic agent along the length of the operative wound.

Referring to FIGS. 3 and 4, which depict the use of the present invention, we see that the aforedescribed catheter is placed percutaneously parallel to and in close proximity to or adjacent to the operative wound (36). The catheter (12) is placed percutaneously in the subcutaneous (38) and muscular (40) planes. The skin (42), fasia (44) and peritoneum (46) are depicted in FIGS. 3 for reference.

In order to place the catheter (12) in position, the obturator (14) is inserted in the tubular member (16) with the end thereof abutting the interior distal end of the tubular member, thus stiffening the catheter. The assembly is inserted into the patient in the appropriate location and the obturator unlocked and removed therefrom. In FIG. 3 and 4 a plurality of catheters are seen adjacent and parallel to the operative wound (36).

After placement of the catheter in the patient, a syringe (48) having a hypodermic needle (50) thereon, is used to inject a local anesthetic agent (52). The local anesthetic agent passes through the catheter (12) and openings (28) therein and disperses into the subeutaneous (38) and muscular (40) planes causing blockage of the segemental nerves (54) and consequent analgesia. The catheter may be removed when no longer needed by placing traction on the luer fitting or hub (24).

It is to be understood that various modifications in the assembly, catheter, obturator and method of analgesia are possible without departing from the scope of the invention and that the description and drawings are illustrative and are not intended to limit the scope of the invention.

What is claimed is:

1. A method of selectively applying continuously or intermittently a local anesthetic along the length of an operative wound comprising:
    inserting a catheter means into the subcutaneous plane and inserting a catheter into the muscular plane, each catheter means substantially parallel to and in close proximity to the wound, each catheter means including means for distributing a liquid injected therein along the length of the wound in said respective plane;
    selectively, intermittently or continuously injecting a local anesthetic agent into each of the catheters to be substantially evenly dispersed along the length of the wound in each of said planes to thereby cause analgesia of the wound.

2. The method of claim 1, wherein the injecting is intermittently.

3. The method of claim 1, wherein the injecting is continuously.